(12) United States Patent
Sharps et al.

(10) Patent No.: US 8,764,691 B2
(45) Date of Patent: Jul. 1, 2014

(54) PANNUS SUPPORT ADAPTED FOR SURGICAL PROCEDURES

(76) Inventors: Paige Long Sharps, Mt. Vernon, NY (US); Janice Hackney, Bronx, NY (US); Harland Abraham, Columbia, MD (US)

(*) Notice: Subject to any disclaimer, the term of this patent is extended or adjusted under 35 U.S.C. 154(b) by 46 days.

(21) Appl. No.: 13/169,717

(22) Filed: Jun. 27, 2011

(65) Prior Publication Data
US 2012/0029295 A1 Feb. 2, 2012

Related U.S. Application Data

(63) Continuation-in-part of application No. 12/844,258, filed on Jul. 27, 2010, now abandoned.

(51) Int. Cl.
*A61F 5/00* (2006.01)
*A61F 5/24* (2006.01)

(52) U.S. Cl.
USPC ............................ 602/19; 602/4; 128/96.1

(58) Field of Classification Search
USPC ........ 128/98.1, 989.1, 100.1, 101, 99.1, 96.1, 128/869, 873, 874, 849, 845, 95.1, 101.1, 128/112.1; 2/44, 45, 92, 311, 312, 330, 2/338, 327, 328; 450/155, 131, 146, 150, 450/114, 115, 117, 118, 120, 122, 123, 124, 450/125, 126, 130; 602/19, 20, 32, 33, 34, 602/35, 36, 37, 38, 4, 60, 61, 67
See application file for complete search history.

(56) References Cited

U.S. PATENT DOCUMENTS

| | | | | | |
|---|---|---|---|---|---|
| 1,828,015 | A | * | 10/1931 | Allebach | 450/113 |
| 5,450,858 | A | * | 9/1995 | Zablotsky et al. | 128/876 |
| 5,503,620 | A | * | 4/1996 | Danzger | 602/19 |
| 6,629,942 | B1 | * | 10/2003 | Tubbs | 602/13 |
| 7,008,292 | B2 | * | 3/2006 | Cosentino et al. | 450/155 |
| 7,156,747 | B2 | * | 1/2007 | Perry | 473/270 |
| 8,066,654 | B2 | * | 11/2011 | Sandifer et al. | 602/19 |

OTHER PUBLICATIONS

Ergodyne 1400UN Back Support Lifting Belt product information, drillspot.com/products/57579/Ergodyne_1400UN_Back_Support_Lifting_Belt, printed prior to Jul. 27, 2010.
Babyhugger Plus One product information, coreproducts.com/asp_catalog/catalog.asp?pca=471, printed prior to Jul. 27, 2010.

* cited by examiner

*Primary Examiner* — Patricia Bianco
(74) *Attorney, Agent, or Firm* — Leason Ellis LLP

(57) ABSTRACT

A pannus support member is configured to support and contain a pannus during a surgical procedure to provide unobstructed access to the surgical site and provide, post surgery, a clean site that is exposed to air to promote proper healing.

13 Claims, 7 Drawing Sheets

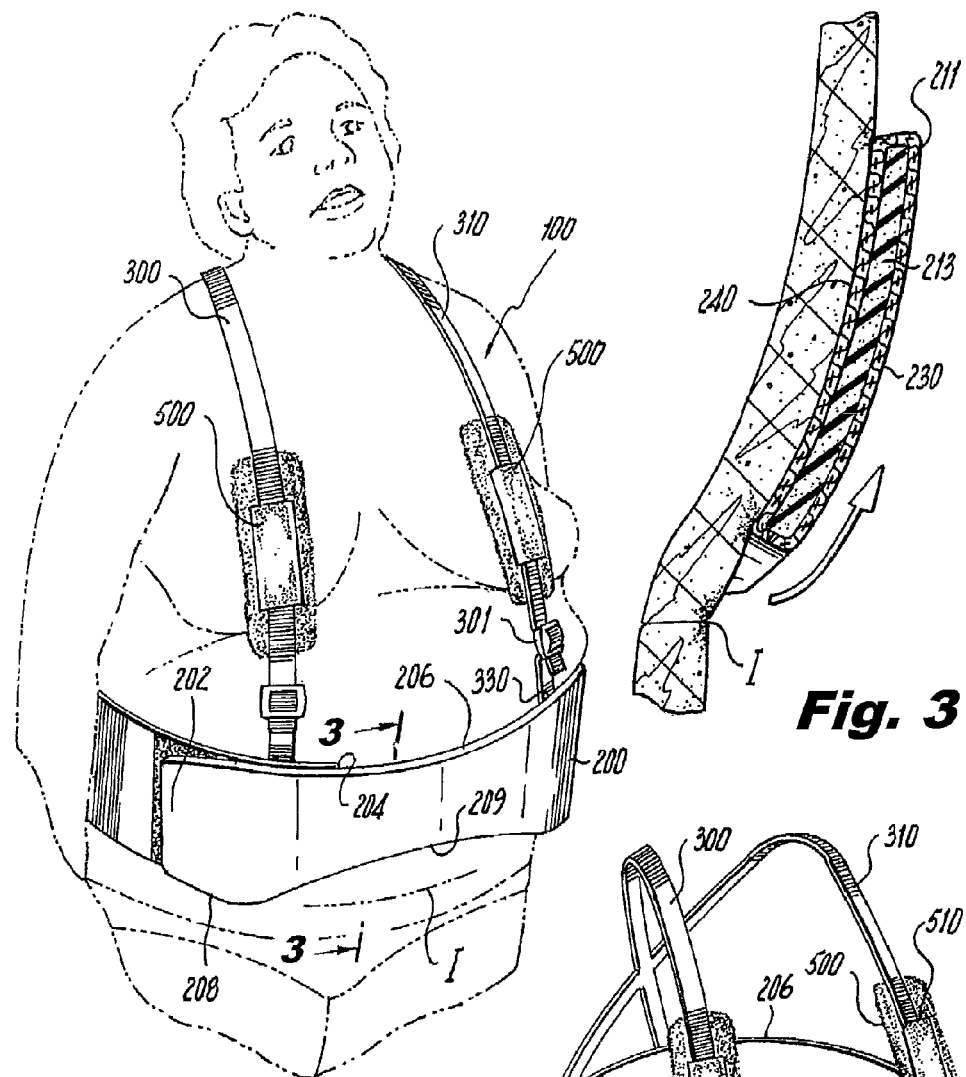
Fig. 1
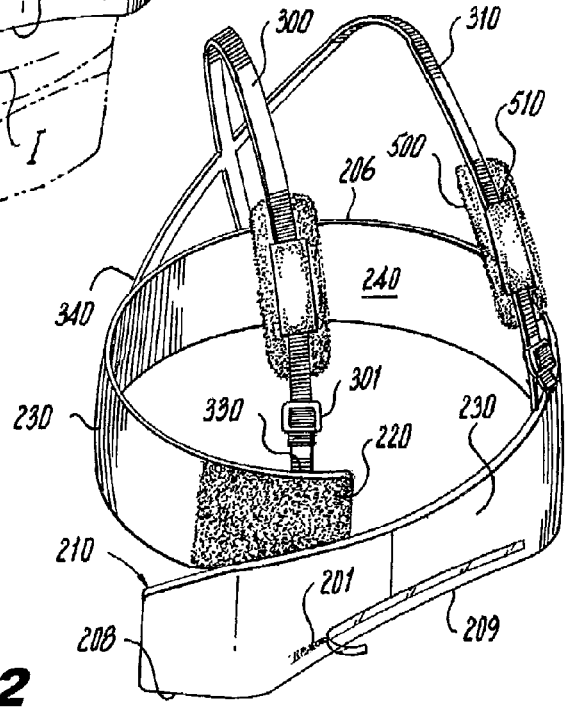
Fig. 3
Fig. 2

PANNUS SUPPORT ADAPTED FOR SURGICAL PROCEDURES

CROSS-REFERENCE TO RELATED APPLICATION

The present application is a continuation-in-part of U.S. patent application Ser. No. 12/844,258, filed Jul. 27, 2010, which is hereby incorporated by reference in its entirety.

TECHNICAL FIELD

The present invention relates to surgical equipment and in particular, to a device that is intended to support and contain a pannus during a surgical procedure to provide unobstructed access to the surgical site and provide, post surgery, a clean site that is exposed to air to promote proper healing.

BACKGROUND

Pannus is a medical term for a hanging flap of tissue. When involving the abdomen, it is called a panniculus and consists of skin, fat, and sometimes contents of the internal abdomen as part of a hernia. A pannus can be the result of loose hanging tissues after pregnancy or weight loss. It can also be the result of obesity which unfortunately is becoming more and more widespread in society. A pannus can come in many different sizes and shapes and can become very large, even hanging down below the knees. The extra tissue of a hanging pannus can make personal hygiene difficult. Skin conditions such as yeast infections under the pannus are common problems since the tissue under the pannus is not properly exposed to air but rather is a warm, moist area where bacteria thrive. A massive hanging pannus can get in the way of walking and prevent a person from performing many of life's daily tasks. A smaller pannus can be an annoyance with clothing as the individual sits or stands.

In term of abdominal panniculi, a grading system has been developed to better assist the physician in classifying the degree of the pannus. The grading system is as follows: grade 1: panniculus barely covers the hairline and mons pubis but not the genitalia; grade 2: extends to cover the genitalia; grade 3: extends to cover the upper thigh; grade 4: extends to cover the mid thigh; and grade 5: extends to cover the knees or beyond.

One situation where a pannus is particularly troublesome and must be properly dealt with is during the delivery of a child from an obese woman. It is generally understood that the term "obese" actually refers to anyone who is more than 30% over their ideal body weight. Obesity can be the result of many factors, including inactivity, poor diet, and certain health-related complications. Obesity is becoming a growing concern among both genders and all age groups. In 1962, 13% of the American population was classified as obese. By 1994, this number had increased to 23%. Yet, just six years later in 2000, this number had skyrocketed to over 30%. Today, an estimated two-thirds of Americans are considered overweight while one in three is obese. As a result, in America, being obese has officially become a marker for classifying a pregnancy as high risk.

Of particular concern for women of childbearing age are the effects that obesity can have on your reproductive health. Obesity put you and your baby at risk for some serious health complications. If a person is obese during pregnancy, the person is at risk of several serious health complications, including: (a) preeclampsia which is a condition which causes high blood pressure, fluid retention, and swelling during pregnancy (When serious, preeclampsia can restrict placental blood flow, endangering baby); (b) gestational diabetes is a form of diabetes that develops during pregnancy and prevents the body from breaking down sugar and can put the baby at risk for gaining too much weight in utero; (c) cesarean section: women who are obese during pregnancy have an increased risk of experiencing problems during delivery and labor is more likely to be slow and prolonged, increasing the likelihood of cesarean section; (d) postpartum infection: Obesity during pregnancy also makes a woman more vulnerable to experiencing a difficult postpartum recovery and in particular, if a woman had a c-section, they are at risk for developing dangerous postpartum infections.

The presence of a pannus during a cesarean section surgical procedure complicates the overall process and additional procedures must be followed to prepare the woman for surgery. As is know, in a conventional cesarean section surgical procedure, after the skin is thoroughly cleansed with an aseptic solution and sterile drapes spread over the surgical field, the abdomen is entered by making an incision through all the layers of the abdominal wall: the skin, the fat and then several muscle layers and muscle sheaths (fascia). This incision can be made either vertically below the umbilicus like a zipper, or horizontally right above the pubic bone, a "bikini cut." Usually all the intestines have been pushed up into the upper abdomen by the enlarged uterus and the uterus lies directly against the abdominal wall. Next, the incision through the muscle wall of the uterus is made and stopped just short of the amniotic sac that contains the baby. The amniotic sac is ruptured carefully, so as not to hurt the baby, and the baby is delivered much as if she were coming out through the vagina.

Recent studies have found that maternity units are not particularly well equipped for obese pregnant women. Presently, fairly crude techniques are used to deal with obese pregnant women that have a pannus that is obstructing the abdomen area where the cesarean section is to be performed. For example, in order to push the pannus back and hold the pannus away from the underlying tissue where the cesarean incision is to be made, an elongated band, such as adhesive tape or the like, is attached to the lower abdomen above the incision on either side and is pulled up and back with sufficient force to lift the pannus away from the underlying tissue, and the other end of the band is fixedly attached to another structure. The structures to which ends of the band are attached can be legs of the bed or other fixtures in the operating room. Once the pannus is lifted, the surgical procedure continues. After delivery of the baby, the incision is closed up and the patient is brought to a recovery room. Unfortunately, the pannus is let to hang back over the incision. As mentioned above, the hanging of the pannus over the incision provides a warm, moist area where bacteria thrive and proper healing is more difficult.

It will be appreciated that while a cesarean section is described herein as being a surgical procedure that is complicated by the presence of a pannus, any surgical procedure where an incision is made in the abdomen or proximate area that is covered by a pannus is equally complicated by the presence of the pannus.

There is therefore a need to provide a pannus support member or adapter that is designed not only to be worn prior to a surgical procedure, such as a cesarean section, but also after it during the recovery period.

SUMMARY

In one embodiment, a pannus support member for lifting and containing a pannus of a patient includes a belt portion for securing around the abdomen of the patient. The belt portion is positioned and is adjustable about the abdomen such that the pannus is contained and lifted by the belt portion away from a target incision area on the abdomen. The pannus support member also includes a pair of straps that are coupled at each end to the belt portion. The pair of straps is constructed to extend across shoulders of the patient and apply a lifting force to the belt portion to cause the pannus to be maintained in a lifted position away from the target incision area. The belt portion includes a bottom edge that has a contoured arcuate shaped front section that is positioned above the target incision area when the belt portion is secured around the abdomen.

In another embodiment, a pannus support member for lifting and containing a pannus of a patient includes a belt portion for securing around the abdomen of the patient. The belt portion is positioned and is adjustable about the abdomen such that the pannus is contained and lifted by the belt portion away from a target incision area on the abdomen. The pannus support member also includes a pair of straps that are coupled at each end to the belt portion. The pair of straps is constructed to extend across shoulders of the patient and apply a lifting force to the belt portion to cause the pannus to be maintained in a lifted position away from the target incision area. A protective cover is detachably attached to a front section of the belt portion and is formed of a liquid impervious material so as to conceal and protect the underlying belt portion in at least the front section.

In yet another embodiment, a method for lifting and maintaining a panniculus in a spaced relationship from the abdomen of a patient includes the steps of: (a) securing a belt portion of a pannus support member around the abdomen of the patient above a target incision area that is located within an abdomen area of the patient, (b) positioning and tightening the belt portion about the abdomen such that the pannus is contained and lifted by the belt portion away from the target incision area; (c) positioning a pair of straps that are coupled at each end to the belt portion across the shoulders of the patient, the pair of straps being constructed to apply a lifting force to the belt portion to cause the pannus to be maintained in a lifted position away from the target incision area; and (d) making an incision in the target incision area, with a bottom edge of the belt portion being located proximate but spaced from the incision.

These and other aspects, features and advantages shall be apparent from the accompanying Drawings and description of certain embodiments of the invention.

BRIEF DESCRIPTION OF THE DRAWINGS

FIG. 1 is a front perspective view of a pannus support member according to a first embodiment being worn by a patient who is in a standing position;

FIG. 2 is front perspective view of another pannus support member;

FIG. 3 is a cross-sectional view taken along the line 3-3 of FIG. 1;

DETAILED DESCRIPTION OF CERTAIN EMBODIMENTS OF THE INVENTION

Figure 4:
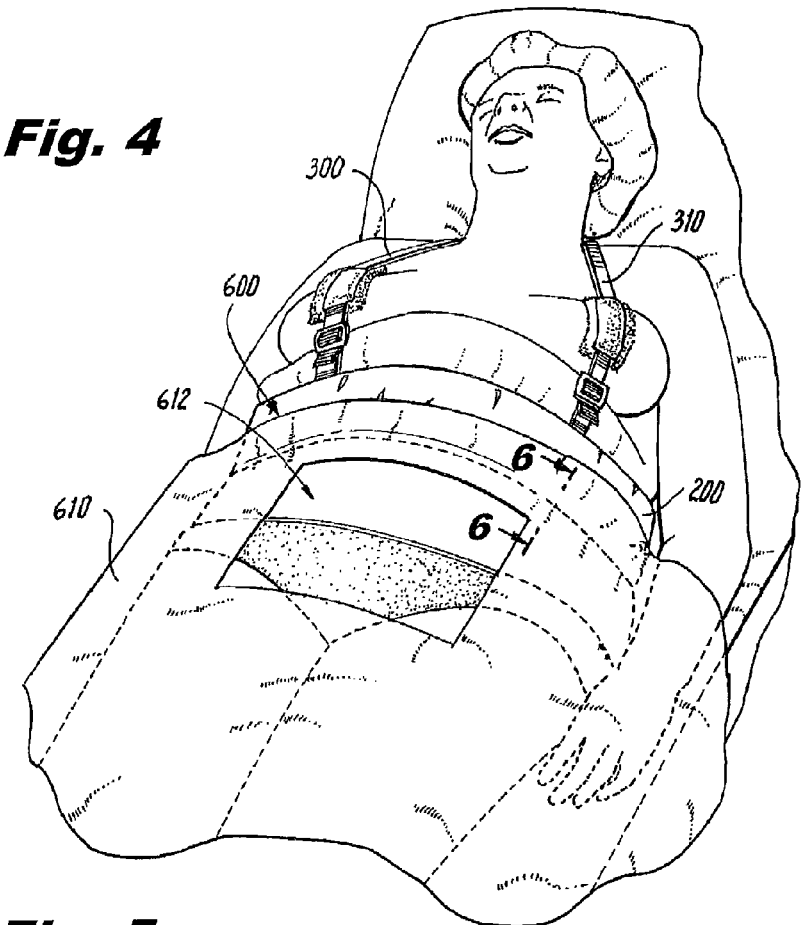
FIG. 4 is front perspective view of a pannus support member according to a second embodiment being worn by a patient who is in a lying position.

FIGS. 1 and 3 illustrate a pannus support member 100 according to one embodiment that is designed to lift and contain a pannus so as to expose the abdomen area to allow a surgical procedure to be performed and to allow proper healing post-surgery.

The pannus support member 100 is formed of a main belt portion 200 that extends around the belly of the wearer and can be adjusted to fit snuggly around the belly. The belt 200 has a first end 202 and an opposite second end 204, with the first end 202 having a first connector 210 (first coupling member) and the second end 204 having a second connector (second coupling member) 220. The first and second connectors 210, 220 are complementary to one another and are configured to mate with one another for attaching the belt portion 200 around the belly. As with most belts, the length of the belt and thus tightness of the belt can be adjusted.

The first and second connectors 210, 220 can be any number of different connectors that are suitable for the intended use. For example, the first and second connectors 210, 200 can be in the form of hook and loop type connectors. In this embodiment, the first connector 210 is one pad formed of hook and loop material formed on an exterior surface 230 of the belt portion 200 proximate the first end 202, while the second connector 220 is another pad formed of complementary hook and loop material formed on an inner surface 240 of the belt portion 200 proximate the second end 204. Hook and loop material connectors 210, 220 permit the length of the belt portion 200 to be adjusted and customized based on the size of the patient and other considerations.

The first and second connectors 210, 220 can also be based on a mechanical type connection and therefore can be in the form of a latch type connector formed of a plastic material. When the first and second connectors 210, 220 are in the form of a latch type connector, the first and second connectors 210, 220 can be located so as not to interfere with the person lying or reclining on a support surface since the pannus support member 100 is intended to be worn on a person that is sitting on a support surface, such as a bed. More specifically, the first and second connectors 210, 220 can be located such that when worn on a person, the first and second connectors 210, 220 are positioned on the hip of the person. In a hip position, the first and second connectors 210, 220 are spaced from the back of the person and likewise are spaced from the front abdomen portion of the person where the surgical procedure is to be performed. On a side, hip portion, the connectors 210, 220 do not interfere with patient sitting and lying down on a surface.

When the first and second connectors 210, 220 are in the form of hook and loop material, the connectors 210, 220 can be located at a rear portion of the belt portion 200 or can be located at a side portion.

The belt portion 200 includes a top edge 206 and an opposing bottom edge 208. The belt portion 200 can have a generally rectangular shape (top edge 206 and bottom edge 208 being parallel) or, as described below, the belt portion 200 can have an irregular shape where one section (e.g., front portion) of the belt portion 200 has a greater width.

The pannus support member 100 also includes a pair of straps 300, 310 are designed to lift the belly and pannus to the shoulders. Each of the straps 300, 310 has a first end 330 that is attached to a front section of the belt portion 200 and a second end 340 that is attached to a rear section of the belt portion 200. The straps 300, 310 are configured so as to provide the necessary lift force that lifts belly and the belt portion 200 for that matter in a direction toward the shoulders.

In one embodiment, the straps 300, 310 are formed of an elastic material and represent elastic bands whose lengths can be extended when a force is applied thereto. The lengths of the elastic material straps 300, 310 are selected so that the straps 300, 310 must be stretched in order to extend across the shoulders of the wearer. Thus, when worn and placed in an elongated condition, the straps 300, 310 store energy and provide the necessary lifting force that causes the pannus to be lifted and contained within the belt portion 200. The combination of the belt portion 200 and the straps 300, 310 contains the pannus within the belt portion 200 and therefore, exposes the abdomen area and permits the incision to be made. In this embodiment, each strap 300, 310 has a single piece construction and can be attached to the belt portion 200 using conventional techniques, including using stitching, etc. In addition, ends of the straps 300, 310 can be attached to the belt portion 200 using hook and loop type material.

In another embodiment, the straps 300, 310 can have an accordion construction to permit stretching of the straps 300, 310 to permit placement of the straps over the shoulders of the wearer. Once again, the straps 300, 310 provide the necessary lifting force for lifting the pannus away from the abdomen.

In yet another embodiment, each strap 300, 310 can be formed of two strap pieces that are attached to one another with a buckle assembly 301 that permits the strap 300, 310 to be tightened and loosed by adjusting the overall length of the strap 300, 310.

For female patients, the straps 300, 310 can include removable, adjustable comfort pads 500 that can be adjusted along the lengths of the straps 300, 310 and are intended to be placed over the breasts of the patient so as to comfort and pad the breasts from the straps 300, 310. The pad 500 can include a slot 510 formed therein to permit the strap 300, 310 to be received therein and permit the pad 500 to be adjusted along the length of the strap 300, 310. A bottom surface of the pad 500 can have a concave surface that seats against the breast. It will also be appreciated that the pads 500 can be used along the shoulders of the person to provide comfort in this region of the patient.

As shown in the figures, the belt portion 200 is constructed to displace the pannus from the surgical area where the incision (I) is made and therefore, the belt portion 200 can be specifically contoured to provide the desired support for displacing and holding the pannus away from the abdomen area but also permit clearance for the incision (I) to be made. For example, the bottom edge 208 can include a concave shaped cutout that defines a concave edge portion 209. The concave edge portion 209 is formed in an area such that when the belt portion 200 is securely attached to itself around the wearer's body, the concave edge portion 209 is positioned over the incision to provide an area of increased clearance for making the incision. In addition, the concave edge portion 209 causes the belt to be spaced even more slightly away from the incision and the fluids that can flow therefrom.

As shown in FIG. 3, the belt portion 200 can be formed of an outer layer 211 (e.g., nylon, etc.) and an inner layer 213 that is typically a padded layer.

As shown in FIG. 1, the pannus support member 100 is constructed and intended to be worn by a patient pre-surgery, during surgery, and post surgery and further is intended to be worn in normal everyday positions, including standing, sitting and lying down.

As shown in FIG. 2, the front section of the belt portion 200 can include a coupling strip 201 that extends along a length of the front section and permits another member (item) to be attached to the belt portion 200. For example, the coupling strip 201 can be in the form of a length of double sided adhesive material that includes a removable release cover to expose the adhesive material. The items that can be attached to the belt portion 200 can be gauze dressing (pads) that extends across the lower edge of the belt portion 200 to provide additional therapeutic benefit to the area of the incision by providing a material that can absorb any fluids, etc., that can create an undesired, moist atmosphere. As discussed herein, the drape (FIG. 4) that is laid over the patient also includes an adhesive backing material and therefore. The drape could cover the coupling strip 201 and therefore, when the drape is placed on the belt portion 200, the drape can be adhesively bonded to the protective cover of the coupling strip 201 and therefore, lifting of the drape will result in lifting of the protective cover. The removal of the drape thus performs two steps, namely, it removes the drape but it also prepares the coupling strip 201 for use by removing the protective cover, thus exposing the underlying adhesive to permit attachment of the gauze material to the belt portion 200.

It will be appreciated that the coupling strip 201 is not limited to being an adhesive material strip.

Figure 5:
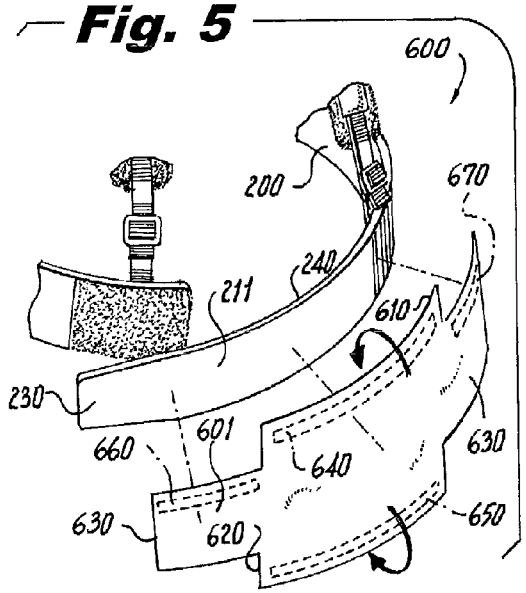
FIG. 5 is an exploded front perspective view of the pannus support member of FIG. 4.
Figure 6:
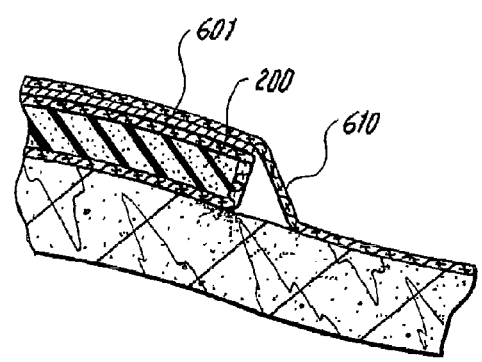
FIG. 6 is a cross-sectional view taken along the line 6-6 of FIG. 4.
Figure 7:
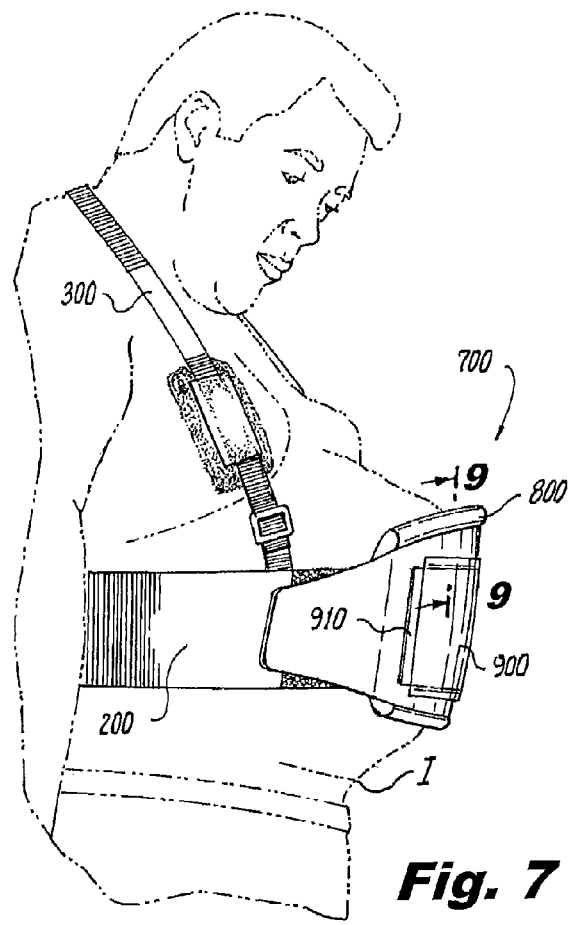
FIG. 7 is a side perspective view of a pannus support member according to a third embodiment being worn by a patient who is in a standing position.
Figure 9:
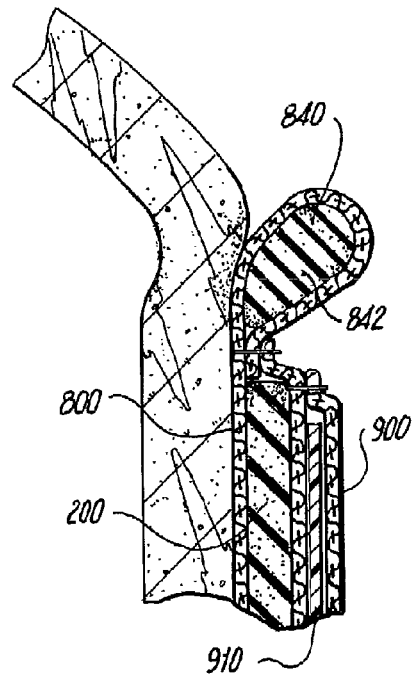
FIG. 9 is a cross-sectional view taken along the line 9-9 of FIG. 7.
Figure 8:
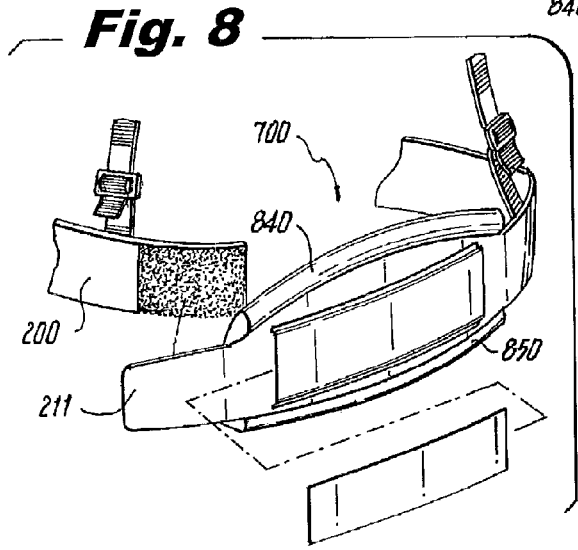
FIG. 8 is a is an exploded partial front perspective view of the pannus support member of FIG. 7.
Figure 10:
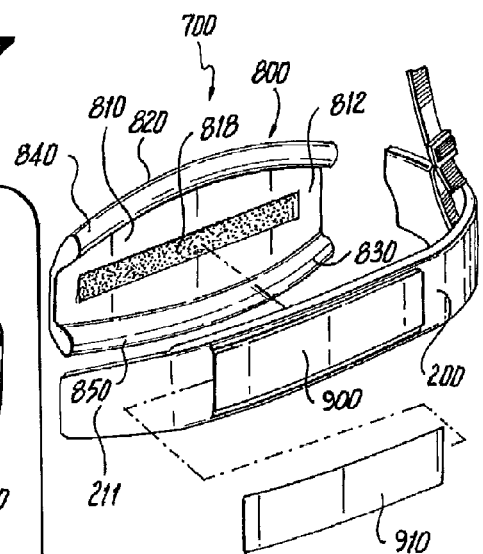
FIG. 10 is a partial front perspective view of the pannus support member of FIG. 7.

Now referring to FIGS. 4-6, a pannus support member 600 according to another embodiment of the present invention is shown. FIG. 4 shows the pannus support member 600 being worn by a patient that is lying on a bed prior to a surgical procedure being performed. A drape 610 is disposed over the patient with a window 612 thereof being aligned with the surgical site, e.g., abdomen or pubic bone area. The drape 610 is formed of a liquid impervious material and includes an adhesive on a backside thereof to permit adhering of the drape 610 to the patient. As is known, the drape 610 can include pockets or the like for capturing the fluid.

As shown in FIG. 4, in the lying down position that is typically for performing a surgery, the pannus support member 600 serves to lift and displace the pannus from the abdomen area, thereby freeing the surgical site and allowing the incision to be made.

The pannus support member 600 is similar to the pannus support member 100 and therefore, like elements are numbered alike. However, the pannus support member 600 has the additional safety feature of having a removable protective cover 601. In accordance with the present invention, the removable protective cover 601 can be provided for protecting at least a front section 211 of the belt portion 200 that is exposed to the surgical site, and potentially may come into contact with fluid and foreign matter, such as blood, amniotic fluid, etc. The protective cover 601 is formed of a suitable material that protects the belt portion 200 from foreign matter, such as fluids from the surgical site. The protective cover 601 is therefore formed of a material that is impervious to fluids and for example, the protective cover 601 can be in the form of plastic sheet (synthetic sheet).

In the illustrated embodiment, the protective cover 601 is at least partially disposed on both the exterior surface 230 and the inner surface 240 of the belt portion 200. In other words, the protective cover 601 extends from the exterior surface 230 to the inner surface 240.

In the illustrated embodiment, the protective cover 601 has a first flap 610 that extends over the top edge of the belt portion 200 to the inner surface 240 and an opposing second flap 620 that extends under the bottom edge of the belt portion 200 to the inner surface 240. The illustrated protective cover 601, the first and second flaps 610, 620 cause the protective cover 601 to have an enlarged center section with two side tabs 630 being formed for placement against the exterior surface 230 of the belt portion 200.

It will be appreciated that the protective cover 601 can be formed using any number of attachment techniques. For example, the cover 601 can be attached to the underlying belt portion 200 using an adhesive material. As shown, a first adhesive section 640 is formed along the first flap 610, a second adhesive section 650 is formed along the second flap 620, a third adhesive section 660 is formed along one side tab 630, and a fourth adhesive section 670 is formed along the other side tab 630. The adhesive sections 660, 670 attached the side tabs 630 to the exterior surface 230 of the belt portion 200, while the adhesive sections 640, 650 attaching the flaps 610, 620 to the inner surface of the belt portion 200.

Alternatively, the protective cover 601 can be attached to the belt portion 200 using stitching in which case, the protective cover 601 is attached along a rupturable tear seam. The user simply pulls the protective cover 601, with sufficient force, to cause rupturing of the tear seam, thereby allowing the protective cover 601 to be removed.

The protective cover 601 is designed to protect the exterior surface 230 of the belt portion 200 from any foreign matter including fluids that result from performing the surgical procedure. It will be appreciated that once the surgery is completed and the patient and surgical area is cleaned and the patient is ready to be delivered to a post-operative location, the protective cover 601 can be removed.

As shown in FIG. 4, the drape 610 is at least partially disposed on the pannus support member 600 and in particular, the drape can be disposed across the front section of the pannus support member 600 including the protective cover 601 thereof. Since the underside of the drape 610 includes an adhesive, the drape 610 is adhesively bonded to the protective cover 601 and therefore, when the drape 610 is removed, the protective cover 601 will also likely be removed therewith. Since the removal of the drape 610 occurs after the surgery is completed and the patient is cleaned, the removal of the protective cover 601 by removal of the drape 610 results in the belt portion 200 being protected from fluids and other foreign matter. Since the protective cover 601 protects the belt portion 200 from foreign material, including fluids, etc., and this permits the pannus support member 100 to be used in a post-operative setting—e.g., while the patient recovers and the incision heals. As a result, the incision area is kept free of the pannus and therefore, the incision area can properly heal since it is exposed to air and can remain clean, can be cleaned, etc. Not only does the pannus support member 600 clear the pannus from the abdomen to allow the surgery to proceed but also provides a much improved recovery period since the pannus is supported and contained by the pannus support member 600 in a manner such that it is kept away from the incision area.

Now referring to FIGS. 7-10, a pannus support member 700 according to another embodiment is illustrated. The pannus support member 700 is similar to the other pannus support members described herein and therefore, like elements are numbered alike. However, in this embodiment, the pannus support member 700 includes a removable accessory 800 that provides additional support and padding for the pannus. The accessory 800 is formed of a body 810 that is complementary to the front section 211 of the belt portion 200 and includes a top edge 820 and an opposing bottom edge 830. The body 810 includes a front surface 812 that mates with the inner surface 240 and also includes a first support and comfort providing member 840 and a second support and comfort providing member 850. The first support member 840 is disposed along the top edge 820 and the second support member 850 is provided along the bottom edge 850. The first support member 840 is not only designed to provide additional support for the pannus but also provides comfort along the top edge 820. In particular, the first support member 840 can include a padded inner material 842 that is surrounded by a cover material that can be the same as and an integral part of the body 810. The first support member 840 can have a rounded shape so as to protect the wearer from a potentially sharp upper edge of the belt portion 200. The support member 840 can be a foam member or it can be an elongated plastic element that is covered by the softer material of the belt material.

The second support member 850 is not only designed to provide additional support for the pannus but also provides comfort along the bottom edge 850. In particular, the second support member 850 can include a padded inner material 852 that is surrounded by a cover material that can be the same as and an integral part of the body 810. The second support member 850 can have a rounded shape so as to protect the wearer from a potentially sharp lower edge of the belt portion 200.

The front surface 812 of the body 810 can include a coupling member 818 that is used to attach the body 810 to the inner surface 240 in a release yet secure manner. For example, the coupling member 818 can be in the form of a piece of hook and loop material that mates with a complementary piece of hook and loop material. Alternatively, the coupling member 818 can be in the form of fasteners, such as buttons, etc.

When the accessory 800 is coupled to the belt portion 200, the first support member 840 extends above and over the upper edge of the belt portion 200 and the second support member 850 extends under and across the bottom edge of the belt portion 200.

The exterior surface 230 of the belt portion 200 can include a pocket 900 for receiving a stiffening member 910. The stiffening member 910 can be formed of a rigid material, such as a rigid plastic insert that is disposed within the pocket 900. The stiffening member 910 adds support and rigidity to the front section of the belt portion 200. This increased rigidity prevents the belt portion 200 from freely rolling or folding over.

In yet another aspect, the belt portion in any of the embodiments can include one or more sections that are formed of anti-microbial material. As is known, anti-microbial material often includes silver ions and is effective against bacteria which are common in a moist, warm area, such as skin of a perspiring person. Preferably, the anti-microbial material contacts the skin when the pannus support member is worn.

In addition, the protective cover used herein can be formed of a material that will change its appearance when exposed to a liquid. For example, the protective cover can change its color when exposed to liquid, thereby alerting the surgical staff that liquid did come into contact with the protective cover during the procedure. Appropriate actions can then be taken including removal of the protective cover.

In yet another embodiment, one or more body coupling members (not shown) can be provided for providing an additional means for attaching the belt portion 200 to the patient's body. The coupling members can be in the form of complementary hook and loop type members (e.g., hook and loop pads), with a first hook and loop pad being attached to the body and a second hook and loop pad being attached to the inner surface 240 of the belt portion 200. For example, the first pad can contain an adhesive layer on one side of the pad (opposite the hook and loop material) that permits the pad to be attached to the patient's body in the abdomen area. The second pad is attached to the inner surface 240 using conventional means such as a bonding material (adhesive) or a mechanical attachment, such as a stitch, etc.

As previously mentioned, it will be appreciated that while a cesarean section is described herein as being a surgical procedure that is complicated by the presence of a pannus, any surgical procedure where an incision is made in the abdomen or proximate area that is covered by a pannus is equally complicated by the presence of the pannus. Accordingly, the pannus support member 100 can be used in other surgical procedures, such as gastric by-pass surgery, appendectomy procedure, gallbladder removal, hysterectomies, etc. As a result, the pannus support member 100 is not limited to being worn by a woman but in some settings and for some surgical procedures, can be worn likewise by a man.

FIGS. 11-17 show a pannus support member 1000 according to another embodiment. The pannus support member 1000 is similar to the pannus support member 100 and therefore, like elements are numbered alike. The pannus support member 1000 is formed of several parts that are complementary to one another and mate with one another. In particular the pannus support member 1000 includes a main belt portion 1010 that is similar to the main belt portion 200 and extends around the belly of the wearer and can be adjusted to fit snuggly around the belly.

Figure 11:
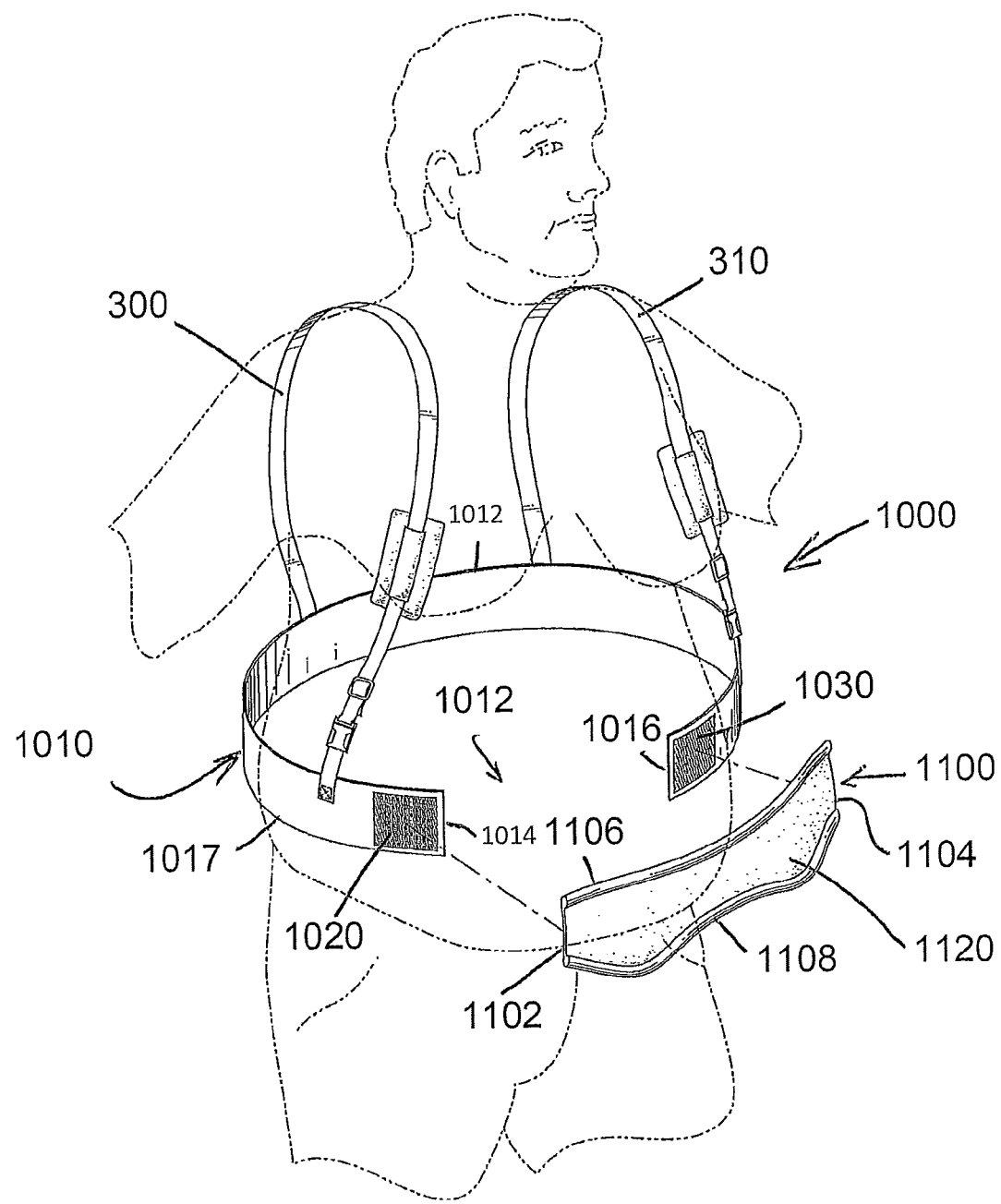
FIG. 11 is a front exploded perspective view of a pannus support member according to a fourth embodiment with a first disposable front belt portion being worn by a patient who is in a standing position.

Unlike the main belt portion 200, the main belt portion 1010 has an open space 1012 formed along the front thereof. FIG. 11 shows the main belt portion 1010 in an open position. The main belt portion 1010 has a first end 1014 and an opposite second end 1016 with the open space 1012 being located between the first end 1014 and the second end 1016. In other words, the main belt portion 1010 is not designed such that the first and second ends 1014, 1016 mate together so as to completely encircle the patient. The main belt portion 1010 is thus designed to be in contact with and cover the back of the patient and it wraps around the hips of the patient but does not completely cover the front of the patient. The ends 1014, 1016 thus do not directly attach to one another.

The main belt portion 1010 can be formed of a soft, comfortable material.

The main belt portion 1010 is constructed so that at or proximate the first end 1014, a first fastening (coupling) member 1020 is provided and at or proximate the second end 1016, a second fastening (coupling) member 1030 is provided. The first and second fastening members 1020, 1030 can be any number of different coupling members, including a wide range of mechanical attachments. For example and as shown, the first and second fastening members 1020, 1030 can be in the form of patches (e.g., square or rectangular shape) of hook and loop material. The first and second fastening members 1020, 1030 are intended, as described below, to mate with a second component that completes the main belt portion 1010.

The main belt portion 1010 includes a top edge 1015 and an opposing bottom edge 1017. The belt portion 1010 can have a generally rectangular shape (top edge 1015 and bottom edge 1017 being parallel) or, as described below, the belt portion 1010 can have an irregular shape where one section (e.g., back portion) of the belt portion 1010 has a greater width.

The pannus support member also includes the pair of straps 300, 310 are designed to lift the belly and pannus to the shoulders. The straps 300, 310 have been described in detail hereinbefore and thus, will not be discussed in further detail. However, it will be appreciated that the ends of the straps 300, 310 can be attached to the main belt portion 1010 using conventional means, such as mechanical fasteners or loops through which the straps 300, 310 are placed and then secured using a mechanical attachment, such as a button or snap or clip, etc. Accordingly, each of the straps 300, 310 has a first end that is attached to a front section of the belt portion 1010 and a second end that is attached to a rear section of the belt portion 1010. The straps 300, 310 are configured so as to provide the necessary lift force that lifts belly and the main belt portion 1010 for that matter in a direction toward the shoulders.

In one embodiment, the straps 300, 310 are formed of an elastic material and represent elastic bands whose lengths can be extended when a force is applied thereto. The lengths of the elastic material straps 300, 310 are selected so that the straps 300, 310 must be stretched in order to extend across the shoulders of the wearer. Thus, when worn and placed in an elongated condition, the straps 300, 310 store energy and provide the necessary lifting force that causes the pannus to be lifted and contained within the main belt portion 1010. The combination of the main belt portion 1010 and the straps 300, 310 contains the pannus within the main belt portion 1010 and therefore, exposes the abdomen area and permits the incision to be made. In this embodiment, each strap 300, 310 has a single piece construction and can be attached to the main belt portion 1010 using conventional techniques, including using stitching, etc. In addition, ends of the straps 300, 310 can be attached to the main belt portion 1010 using hook and loop type material.

As mentioned above, the pannus support member 1000 includes a second component or part 1100 that mates with the main belt portion to complete the belt and can thus be thought of as being a front belt portion. The second component 1100 is designed to be a disposable member. The second component 1100 is designed to be disposed within the open space 1012 between the free ends of the main belt portion 1010.

The second component 1100 is thus in the form of an elongated patch or front belt portion that has a free first end 1102, a free second end 1104, a top edge 1106, and a bottom edge 1108. The second component 1100 also includes a first face 1110 that faces inward toward the patient and a second face 1120 that faces outward away from the patient. The second component 1100 is preferably formed of a soft material and can be the same material as the material that forms the main belt portion 1010.

Figure 13:
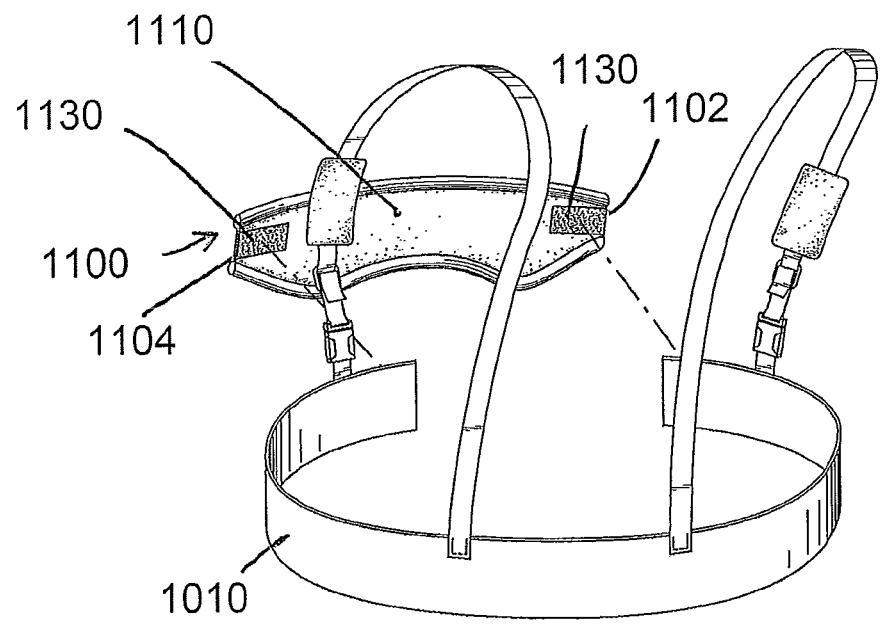
FIG. 13 is a rear perspective view of the pannus support member of FIG. 11.

As shown in FIG. 13, the first face 1110 includes a pair of fastening (coupling) members 1130 that are complementary to the first and second fastening members 1020, 1030. The members 1130 and members 1020, 1030 engage one another so as to attach the first end 1102 to the first end of the main belt portion 1010 and the second end 1104 to the second end of the main belt portion 1010. In the illustrated embodiment, the fastening members 1130 are in the form of sections of hook and loop material at the ends of the second component 1100.

Figure 17:
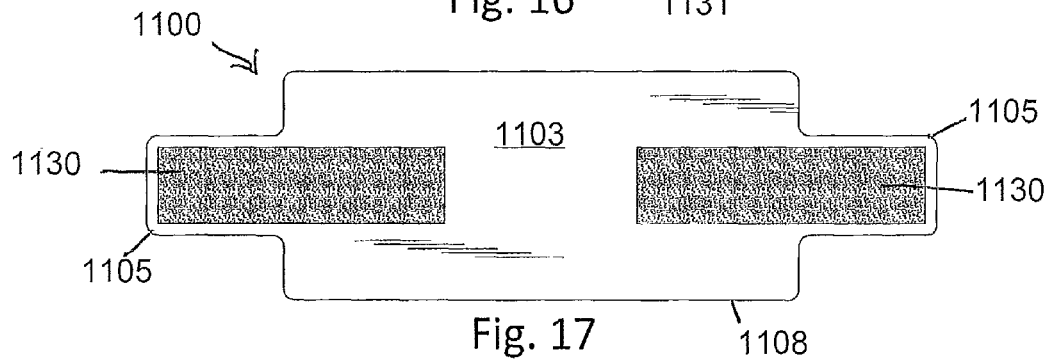
FIG. 17 is a rear elevation view of an alternative front belt portion.

As shown in FIG. 17, in one embodiment, the second component 1100 includes a center section 1103 and a pair of side extensions 1105 that extend outwardly from the ends of the center section 1103 and define the ends of the second component 1100. The extensions 1105 are the portions on which the fastening members 1130 are formed such that these fastening members 1130 are the portions of the second component 1100 that are securely attached to the main belt portion 1010.

The second component 1100 is intended for a pre-operative environment and after the surgery is performed, the second component 1100 can then be discarded. Since the second component 1100 is intended for the pre-operative environment, the bottom edge 1108 of the second component 1100 can be curved (arcuate). The curved bottom edge 1108 is thus positioned adjacent the incision and the curvature allows easy access to the incision area, while maintain the structural integrity and robustness of the belt.

Figure 12:
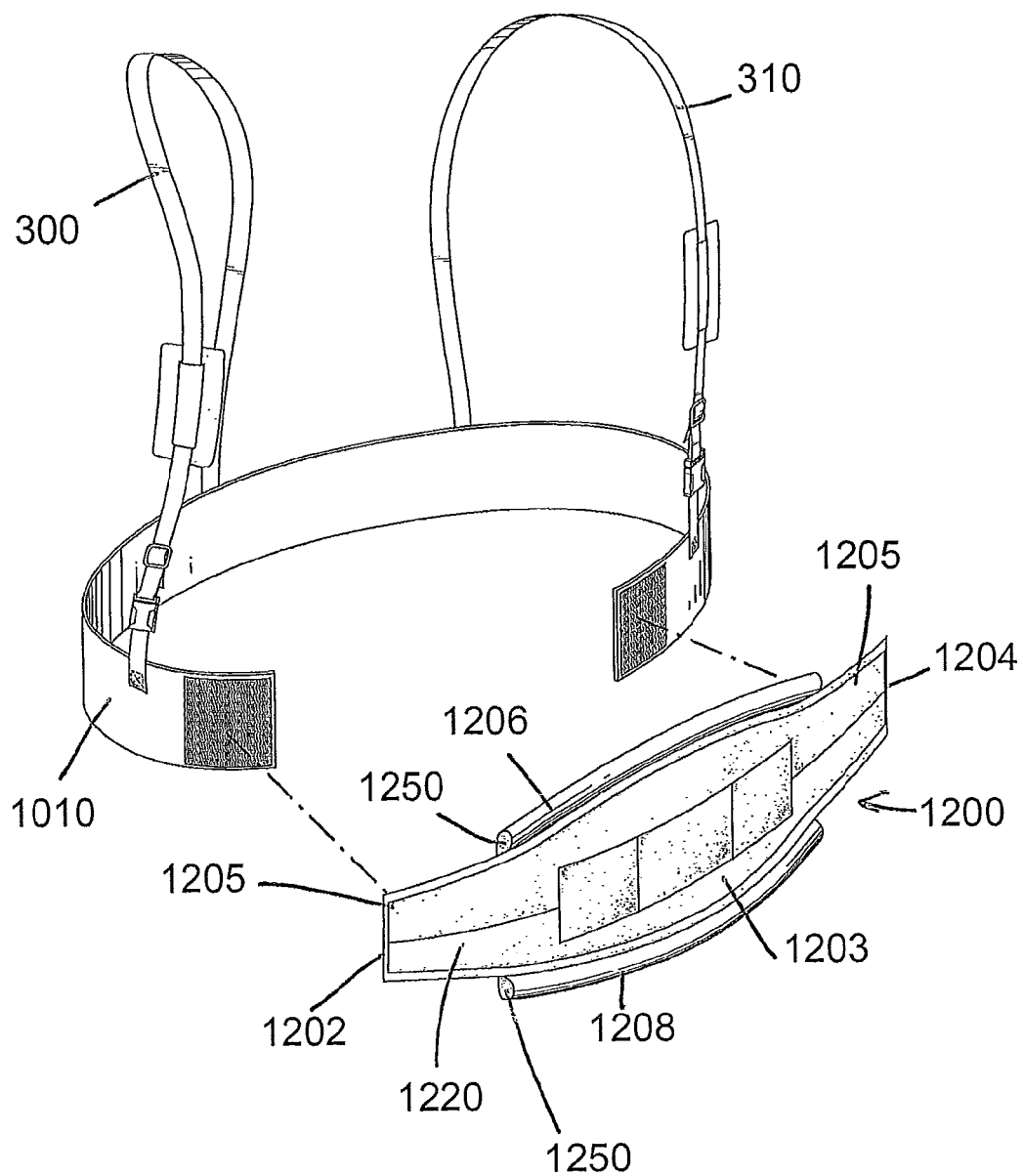
FIG. 12 is a front exploded perspective view of a pannus support member of FIG. 11 with a different second disposable front belt portion.
Figure 14:
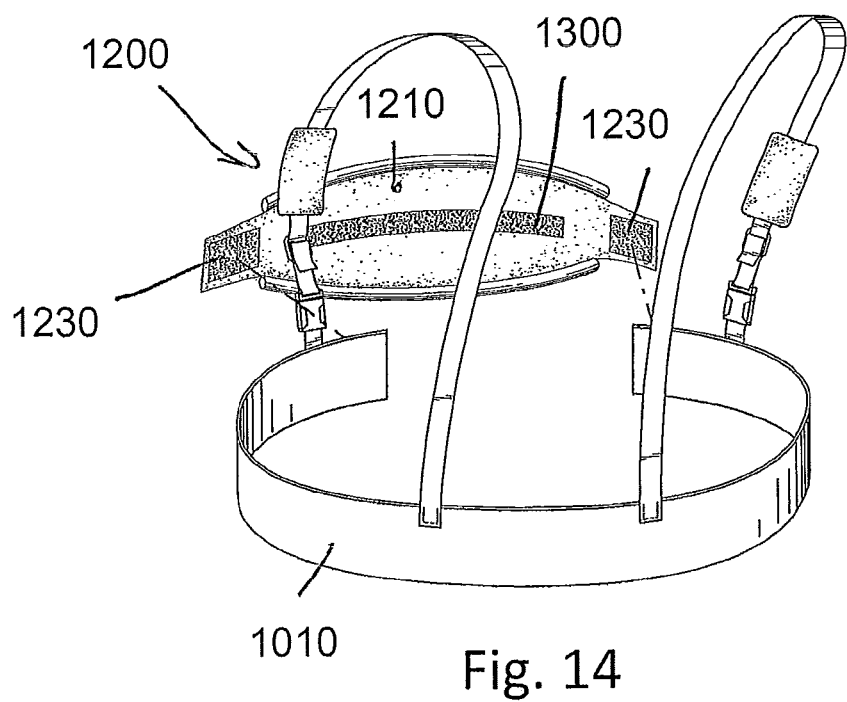
FIG. 14 is a rear perspective view of the pannus support member of FIG. 12.

In yet another aspect of the present invention, the pannus support member 1000 can be part of a kit and can include more than one type of disposable front belt portion (second component 1100). More specifically, different types of disposable front belt portions can be used depending upon the precise environment and intended application. For example, the second component 1100 is intended for use in a pre-operative environment, while FIGS. 12 and 14 show an alternative second component 1200 that is intended for use in a post-operative environment after the surgery has been completed. The second component 1200 is thus also intended for use at home or at the place of recovery and is intended to be worn for an extended period of time as discussed hereinbefore and thus can provide some addition features and comfort relative to the second component 1100 which is only intended for use for a short time prior to and during the surgical procedure.

The second component 1200 is similar to the second component 1100 in that it is a front belt portion or patch that completes the main belt portion 1010. The second component 1200 mates to the main belt portion 1010 so as to form a releasable attachment therebetween, thereby allowing disposal of the second component 1200.

The second component 1200 includes a free first end 1202, a free second end 1204, a top edge 1206, and a bottom edge 1208. The second component 1200 also includes a first face 1210 that faces inward toward the patient and a second face 1220 that faces outward away from the patient. The second component 1200 is preferably formed of a soft material and can be the same material as the material that forms the main belt portion 1010.

The first face 1210 includes a pair of fastening (coupling) members 1230 that are complementary to the first and second fastening members 1020, 1030. The members 1230 and members 1020, 1030 engage one another so as to attach the first end 1202 to the first end of the main belt portion 1010 and the second end 1204 to the second end of the main belt portion 1010. In the illustrated embodiment, the fastening members 1230 are in the form of sections of hook and loop material at the ends of the second component 1100.

In the illustrated embodiment, the second component 1200 includes a center section 1203 and a pair of side extensions 1205 that extend outwardly from the ends of the center section 1203 and define the ends of the second component 1100. The extensions 1205 are the portions on which the fastening members 1230 are formed such that these fastening members 1230 are the portions of the second component 1200 that are securely attached to the main belt portion 1010.

Figure 15:
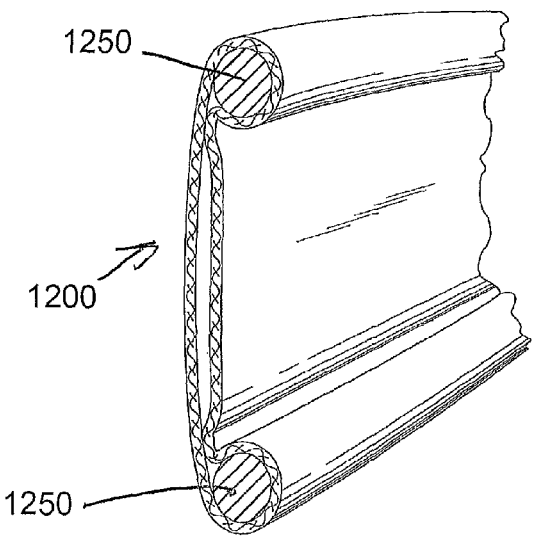
FIG. 15 is a cross-sectional view of the front belt portion of FIG. 14.
Figure 16:
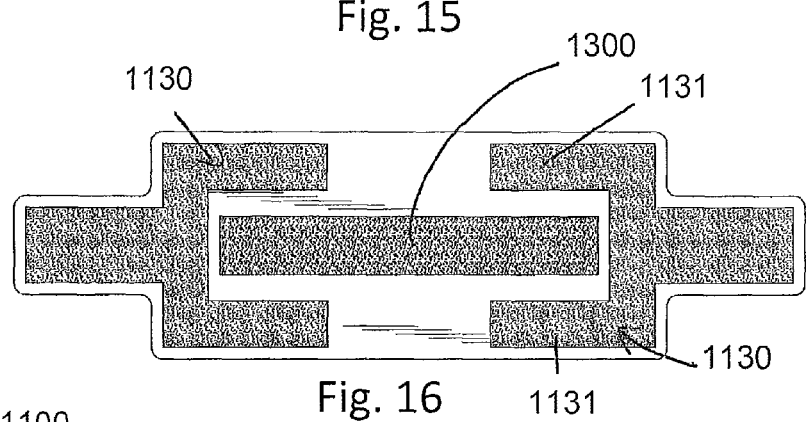
FIG. 16 is a rear elevation view of an alternative front belt portion.

Since the second component 1200 is intended for use in a post-operative environment, the second component 1200 can include additional structural support members. For example, along the top edge 1206 and the bottom edge 1208, reinforcing members 1250 can be provided to provide increased support and robustness in these areas. The reinforcing members 1250 can and preferably are formed of a material that is different than the material that is used to form the other main sections of the second component 1200. For example as shown in FIG. 15, the reinforcing members 1250 can be in the form of elongated members, such as plastic rods, that are disposed within a pocket that extend along the top and bottom edges or is other attached to the second component 1200 along the top and bottom edges thereof. The reinforcing members 1250 are covered with the material of the second component 1200 so as to provide padding over the harder, more rigid reinforcing members. The reinforcing members have some flexibility to allow the second component 1200 to bend and accommodate and mirror the curved shape of a patient's body.

The reinforcing members 1250 generally have lengths that correspond to the length of the center section 1203. The extensions 1205 thus extend beyond the ends of the central section 1203 and the reinforcing members. As explained above with reference to element 840, the reinforcing members 1250 provide support for the pannus, while being designed to still maintain comfort.

As explained above, an adhesive 1300 can be provided on the second face of the second component 1100, 1200 to assist in the attachment of the second component 1100, 1200 to the patient's body (skin). For example, in FIG. 16, the adhesive 1300 can be disposed along the second face. In addition, in this illustrated embodiment, the fastening members 1130 can be each formed such that the fastening member 1130 at least partially surrounds the adhesive 1300. For example, the fastening member 1130 can include a pair of legs 1131 that are parallel to one another and spaced apart (e.g., U-shaped) to define a space that receives one end section of the adhesive 1300. This permits a longer section of adhesive 1300 to be used when desired. The adhesive 1300 has a protective cover (release layer) that is removed prior to use.

It is preferred that the pannus support member 1000 be provided as part of a kit that includes the two different types of second components 1100, 1200 (front belt portions) that complete the main belt portion 1010 and are disposed proximate the incision and further, are located where the pannus is present and requires support. Thus, the kit can be provided and be packaged in a single package that is opened at the surgical site (e.g., a hospital). The second component 1100 then used in the pre-operative and surgical environments and then after the surgical procedure is completed, the second component 1100 is removed and the second component 1200 is then used and is attached to the main belt portion 1010. The patient can thus be sent home wearing the second component 1200 with instructions to wear the pannus support member 1000 with the second component 1200 for an extended period of time.

To attach the pannus support member 1000 to the patient, the main belt portion 1010 is placed around the back and hips of the patient with the free ends 1014, 1016 of the main belt portion 1010 being generally positioned in the front of the patient. The straps 300, 310 are then placed over the shoulders of the patient as described above and are secured to the main belt portion 1010.

The ends 1014, 1016 of the main belt portion 1010 are disposed across the front of the patient with the space 1012 being generally centrally located along the front of the patient.

First, the second component 1100 is then attached to the main belt portion 1010 is by positioning the first face 1110 toward the patient. The fastening member 1130 at the first end 1102 is then attached to the fastening member 1020 so as to couple the second component 1100 to the main belt portion 1010. The second component 1100 is than placed across the patient's body such that the pannus is located above its top edge (thus, the second component 1100 supports the pannus). The second end 1104 of the second component 1100 is then stretched across the patient's body such that the fastening member 1130 of the second end 1104 is mated to the fastening member 1030 of the main belt portion 1010.

The surgical procedure is then performed as discussed above.

After the surgical procedure is completed, the second component 1100 is removed and then the second component 1200 is installed in the same manner as to how the second component 1100 is installed. The second component 1200 is intended for extended wear.

Since the second component 1100, 1200 is freely removable, the second component can easily be detached in case or need of cleaning and/or replacement. In addition, different style second components 1200 can be available for use and therefore, the user can easily purchase a different second component 1200 for use. For example, the degree of padding for the second component 1200 can be varied and/or the characteristics of the reinforcing elements can be varied.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A pannus support member for lifting and containing a pannus of a patient comprising:
   a main belt portion for securing around the abdomen of the patient;
   a disposable first front belt portion that is intended for wearing prior to and during surgery and is detachably secured at two opposing ends to the main belt portion in such a way that the first front belt portion can be completely detached and removed from the main belt portion by solely detaching the two opposing ends of the front belt portion from the main belt portion to allow disposal thereof after surgery, the first front belt portion and the main belt portion forming an assembled belt when the first front belt portion and the main belt portion are attached to one another, the assembled belt being positioned and adjustable about the abdomen such that the pannus is contained and lifted by the main belt portion and the first front belt portion away from a target incision area on the abdomen, the first front belt portion having a bottommost edge that has a contoured concave shaped front section that is centrally located for positioning above the incision area of the abdomen when the assembled belt is secured around the abdomen;
   a second front belt portion that comprises a post-operative belt portion that is worn post surgery, the second front belt portion being detachably secured at two opposing ends to the main belt portion in such a way that the second front belt portion can be completely detached from the main belt portion to allow disposal thereof, the second front belt portion and the main belt portion forming an assembled belt when the second front belt portion and the main belt portion are attached to one another, the assembled belt being positioned and adjustable about the abdomen such that the pannus is contained and lifted by the main belt portion and the second front belt portion away from an incision area on the abdomen, wherein the second front belt portion has a different construction relative to the first front belt portion, the second front belt portion having a bottom edge that has a contoured convex shaped front section that is positioned above the incision area when the assembled belt is secured around the abdomen; and
   a pair of straps that are coupled at each end to the belt portion, the pair of straps being constructed to extend across shoulders of the patient and apply a lifting force to the belt portion to cause the pannus to be maintained in a lifted position away from the incision area.

2. The pannus support member of claim 1, wherein the second front belt portion includes a plurality of reinforcing elements, with one being disposed along a top edge and one along a bottom edge thereof.

3. The pannus support member of claim 2, wherein the reinforcing members comprise tubular plastic members.

4. The pannus support member of claim 2, wherein the second front belt portion comprises pockets that extend along the top and bottom edges thereof, the reinforcing members being disposed inside the pockets.

5. The pannus support member of claim 1, wherein the main belt portion and the first front belt portion is formed substantially of a fabric material.

6. The pannus support member of claim 1, further including a pair of straps that are coupled at each end to the main belt portion, the pair of straps being constructed to extend across shoulders of the patient and apply a lifting force to the belt portion to cause the pannus to be maintained in a lifted position away from the target incision area, wherein each strap is formed of an elastic material that stretches and stores energy when the patient wears the pannus support member, thereby generating the lifting force.

7. The pannus support member of claim 1, further including a pair of straps that are coupled at each end to the main belt portion, the pair of straps being constructed to extend across shoulders of the patient and apply a lifting force to the belt portion to cause the pannus to be maintained in a lifted position away from the target incision area, wherein each strap has an adjustable length to permit adjustment to generate the lifting force.

8. The pannus support member of claim 7, wherein each end of the first front belt portion includes hook and loop material that mates with hook and loop material that is associated with the end portion of the main belt portion.

9. The pannus support member of claim 1, wherein each end of the first front belt portion overlaps an end portion of the main belt portion and is securely coupled thereto.

10. The pannus support member of claim 1, wherein the main belt portion has two free ends with each end including first fastening members and ends of the first front belt portion includes second fastening members for detachably securing the first front belt portion to the main belt portion.

11. The pannus support member of claim 10, wherein the first and second fastening members comprise snap-fit attachments.

12. The pannus support member of claim 10, wherein the first front belt portion includes a center section and a pair of side extensions that extend outwardly therefrom, the second fastening members being disposed along the side extensions.

13. The pannus support member of claim 10, wherein the first and second fastening members comprise sections of hook and loop material.

* * * * *